United States Patent
Koenig (10) Patent No.: US 7,526,132 B2
(45) Date of Patent: Apr. 28, 2009

(54) APPARATUS, METHOD, STORAGE MEDIUM AND DATA STRUCTURE FOR IDENTIFYING AND STORING DATA

(75) Inventor: Helmut Koenig, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 981 days.

(21) Appl. No.: 10/753,370

(22) Filed: Jan. 9, 2004

(65) Prior Publication Data

US 2004/0162809 A1 Aug. 19, 2004

(30) Foreign Application Priority Data

Jan. 9, 2003 (DE) ................. 103 00 545

(51) Int. Cl.
*G06K 9/36* (2006.01)
*G06K 9/46* (2006.01)
(52) U.S. Cl. ..................... 382/232
(58) Field of Classification Search ............... None
See application file for complete search history.

(56) References Cited

U.S. PATENT DOCUMENTS

| | | | | |
|---|---|---|---|---|
| 5,724,582 A | * | 3/1998 | Pelanek et al. .......... 707/204 |
| 5,926,576 A | * | 7/1999 | Newton ................ 382/247 |
| 5,940,585 A | * | 8/1999 | Vondran et al. .......... 358/1.15 |
| 6,002,814 A | * | 12/1999 | Chadez ................ 382/303 |
| 6,298,173 B1 | * | 10/2001 | Lopresti ................ 382/305 |
| 6,604,158 B1 | * | 8/2003 | Fallon ................... 710/65 |
| 2003/0044076 A1 | * | 3/2003 | Mitchell et al. .......... 382/239 |
| 2004/0141661 A1 | * | 7/2004 | Hanna et al. ............. 382/305 |

OTHER PUBLICATIONS

Picture Publisher 4.0: Automatisieren mit Makors. In: Zeitschrift Vollversion, Ausgabe Nr. 102, Zweitauslieferung Feb. 2000, S. 56.
Picture Publisher 4.0: Spezialeffekte. In: Zweitauslieferung Feb. 2000, S. 59-61.

* cited by examiner

*Primary Examiner*—Matthew C Bella
*Assistant Examiner*—Yuzhen Ge
(74) *Attorney, Agent, or Firm*—Harness, Dickey & Pierce, P.L.C.

(57) ABSTRACT

An apparatus, a method, a data structure and a storage medium with a program are for identifying and storing image data and/or metadata. The apparatus includes an electronic data processing device for the processing of the data by a user. It furthermore includes an electronic data management device, which can bring the data to a format suitable for storage, and a storage device for storing the data. A data loss check device can check the processed data for data loss in comparison with the original data. The data can be identified by the data management device in a manner dependent on the result of such a check. Lossy data are stored by the storage device in addition to data obtained in a lossless manner.

10 Claims, 3 Drawing Sheets

FIG 1

FIG 2

APPARATUS, METHOD, STORAGE MEDIUM AND DATA STRUCTURE FOR IDENTIFYING AND STORING DATA

The present application hereby claims priority under 35 U.S.C. §119 on German patent application number DE 103 00 545.5 filed Jan. 9, 2003, the entire contents of which are hereby incorporated herein by reference.

FIELD OF THE INVENTION

The invention generally relates to an apparatus, a method, a storage medium and/or a data structure for identifying and storing image data. In particular, the image data may include medical image data and/or metadata. Further, an electronic data processing device may be used for the processing of the data by a user and an electronic data management device and storage device may be used for storing the data.

BACKGROUND OF THE INVENTION

Image data, in particular medical image data, may be generated by a number of types of image recording devices, e.g. by computer tomographs, X-ray devices or ultrasound devices. They may be used in medical diagnosis, in material examinations or in material sciences. Image data of this type are increasingly being electronically processed and stored.

Moreover, metadata, such as items of information on the identity of an examined person or an examined object, diagnostic or analytical findings with respect to the images or further commentarial information items, are often added to the data to be stored. The metadata may be present in the form of text or numbers. They may be added either automatically or by a user.

Image data and metadata, once they have been stored, can be post-processed at any time after the first, original storage and be stored anew. In the context of instances of post-processing, it is possible, on the one hand, to amplify or clarify constituent parts of an image. Further, it is possible, on the other hand, to alter or erase constituent parts of an image.

The same, in principle, applies to the metadata, the information content of which can be both supplemented and revised after it has been generated for the first time. Overall, the stored information can thus be revised either in a loss-less manner or in a lossy manner, wherein some information is lost. The lossy revision of information is to be regarded as critical, principally when the recovery of the original information is either impossible or possible only by a reexamination of the person or of the object by an examination device that is possibly not free of side effects or not nondestructive.

However, data losses are not desirable with regard to other items of information as well. A main concern in the storage of medical or analytical image data must therefore lie in ensuring that data, once they have been obtained, are retained in a lossless manner. Furthermore, a patient or examination history can be obtained through the lossless retention of information recorded in chronological succession.

Conventional methods for preventing original, lossless data from being erased or overwritten are based on a so-called archive bit being added to the files which contain these data. The term archive bit refers to an identification which identifies the data as archive data which are intended to be stored permanently as such, but without the possibility for alterations. A further conventional possibility includes adding to the data, as they are being used, an identification as "processed" or, "unprocessed". However, this identification merely gives information about whether an alteration of whatever kind has been made to the data, but without taking account of the type and extent of the alteration. By way of example, changing the contrast or the brightness of image data, which would not alter the actual information content thereof, would already lead to such data being identified as altered.

A data management system which has to ensure that original data are retained in a lossless manner could operate on the basis of conventional data identifications only in such a way that it would store in each case separately all the data identified as archive data or as "processed". As a result, although the lossless retention of original data would be ensured, a multiplicity of data which have merely been subjected to unimportant changes would also likewise be additionally stored and retained.

This multiplicity of data records stored more or less unnecessarily would on the one hand generate an unnecessarily high storage space requirement, which would rapidly assume untenably large dimensions, particularly in the case of extensive image data. On the other hand, the user who is supposed to work with these data would be overloaded with a flood of insignificant information, which would make practical utilization of the databases and the evaluation of the data history considerably more difficult and virtually impossible for everyday use. In a similar manner to that for image data, this would also apply to text information in the metadata, in which case the storage space requirement is quite generally to be regarded as noncritical.

A data management system which is intended to ensure the lossless retention of all information would be compelled to separately store every revised version of a findings or analysis text. Thus, it would be necessary for example also to store text versions in which all that has been changed is the text format and typeface, but not the information content. For the user, who wishes primarily to utilize the information content, it would be unnecessarily complicated and confusing to have to check different versions of the text in respect of whether merely structural alterations or else alterations to the content have been made.

Finding differences can be complicated and difficult enough even when using different versions of data having altered contents, whether they be image data or text data. Although it is known for text changes and commentaries to be emphasized e.g. by color highlighting, the emphases do not distinguish between changes to contents and structural changes; moreover, the history of the text information across a number of versions cannot be represented in user-friendly fashion. In such a system, it would be left to the user to store only new versions having revised contents as new data records, in order to prevent the creation of a multiplicity of text versions which have matching contents and have only been altered editorially. It would likewise be left to the user to mark changes to contents in such a way that the history of a multiply revised text remains readily understandable and comprehensible for subsequent consideration.

The above-described problems of the lossless retention of original image data and metadata, the storage of such data with a comprehensible processing history and the restriction to a tenable storage space requirement occur particularly with medical diagnosis image data. In this case, image data which reproduce the status of a patient at a specific point in time are obtained by means of imaging methods. Depending on the imaging method, the image data have a high resolution and are very extensive and therefore require an extremely large amount of storage space. The repeated recording of such image data is quite generally not possible at arbitrary later points in time owing to the continual alteration of the patient status.

The image data from imaging methods are supplemented by metadata, which may contain, usually in the form of text statements on the patient's subjective wellbeing, medial findings or the supplementary information on the illness history. In the same way as the image data, the medically relevant metadata cannot readily be reconstructed later, since both the patient's subjective perception and the patient's illness history change with time. Moreover, a medical point of view that has changed with time may lead to different findings.

Furthermore, it is necessary precisely in the case of medical data to enable an assessment at later points in time or by other medical experts, e.g. in the context of the medical documentation obligation or in the case of use in a knowledge-based system. This presupposes the retention of lossless original data in the case of different instances of processing in the same way as a tenably low storage outlay for the purpose of sufficiently rapid processing and also a representation of the temporal evolution of the data which is comprehensible in a user-friendly manner.

SUMMARY OF THE INVENTION

An aim of an embodiment of the invention is to store image data and associated metadata with the original, complete information content in loss-proof fashion, to protect them from being erased and overwritten, and to store revised versions of the data likewise in loss-proof fashion and to enable their later repeated user-friendly processing whilst taking account of the temporal genesis of image data and metadata. At the same time, an embodiment of the invention aims to keep the associated storage space requirement at a low level and to reduce the quantity of insignificant information that is a hindrance to later processing.

An embodiment of the invention may achieve an aim by an apparatus, a method, a data structure and/or a storage medium.

One basic concept of an embodiment of the invention includes storing original image data, that is to say raw image data or image data that have been reconstructed in a standardized manner on the basis thereof and optionally processed afterward, and also original metadata. Further, revised versions of the data may be checked with regard to data losses and they may be identified based upon the result of this check. Further, they may be stored together with the identification, with data revised in a lossy manner being stored in addition to data obtained in a lossless manner. In this case, the terms "standardized" reconstruction and processing of the raw data relate to recommendations and specifications of experts, in particular of medical experts (e.g. the American College of Radiology) for the processing of data.

Thus, raw data may be preserved in terms of their complete information content and, if need be, can be overwritten by data that are equivalent in terms of their information content. By contrast, revised data with a changed information content are stored separately, if appropriate, in addition to the lossless data. Subsequently revised versions of the data are likewise checked with regard to data losses, identified as lossless or lossy and stored or additionally stored in a manner dependent thereon.

As a result, an embodiment of the invention provides for the lossless retention not only of the raw data but also of every revised version of the data. Through the retention of every revised version of the data, the complete genesis is simultaneously preserved and can be comprehended afterward. Moreover, dispensing with the additional storage of data that are unaltered in terms of their information content additionally achieves a considerable reduction of the storage requirement.

One aspect of an embodiment of the invention resides in the determination of alterations of the information content of the image data and metadata. In order to be able to perform a corresponding identification, alterations which are relevant to the information content have to be distinguished from irrelevant alterations. For this purpose, in a particularly advantageous variant, an embodiment of the invention uses a knowledge-based system which is suitable for examining alterations of data in respect of whether they are connected with alterations of the information content. On the basis of a check of the data by the knowledge-based system, the system allocates corresponding identifications for altered data and decides whether these data are to be stored by overwriting existing data or as supplementary data records. During the evaluation of the alteration to image data and metadata, the knowledge-based system relies on various facts and rules which can be interpreted as logically and physically separable knowledge bases and inference machines. This is because while image data involve the alteration of individual pixels, the information content of information elements such as letters, whole words or sentences is examined in the case of metadata, in particular in the case of text data.

One advantageous refinement of an embodiment of the invention resides in the fact that, in the event of alteration of the data, not only the amended versions, if appropriate, of the data are stored, but also the operations by which amended versions were produced. As a result, the origination of the respective data state may be comprehended afterward, which may be useful particularly in the case of image data. Moreover, the storage space requirement may thereby be reduced in that only operations for the alteration of the original image data are stored instead of complete revised images.

A further advantageous refinement of an embodiment of the invention resides in the fact that an identification concerning the updated nature of the respective data state is stored together with the respective data. By storing the data e.g. with the processing or origination date of the respective data record, the genesis of the data remains reconstructable and comprehensible afterward.

A further advantageous variant of an embodiment of the invention results by virtue of the system optimizing the storage performance when storing the relevant data that have been recognized as needing storage by virtue of the selection of storage formats with a low storage outlay and at the same time a low time outlay in the event of access and reproduction of the stored data. In order to increase the storage performance, the system, in one embodiment, is provided with a further knowledge-based system which is suitable for determining a most favorable storage format in each case. While the minimization of the storage requirement is known per se in the storage of image data, the knowledge-based system serves in particular for simultaneously optimizing the access speed or reconstruction time of revised image data.

In order to be able to enhance the storage of the revised image data, the system records the operations or graphical processing steps performed during the revision of the image data and examines them with regard to whether the storage of the altered image data would ensure a better storage performance than the storage of the individual graphical processing steps. The fact of whether the revised image data or the graphical operations which represent the sequence of the processing steps are stored is decided on the basis of the rules of the knowledge-based system. In this case, the knowledge-based system takes account of the interaction between storage performance and the representation or processing performance during the later processing or reconstruction of the stored data. Thus, either the unprocessed data and also the associated processing steps are stored, or else the processed data, depending on whether the time and storage outlay for the subsequent reconstruction, that is to say for representation and access, turns out to be lower or higher in the overall weighing up.

The knowledge-based system of one embodiment, for enhancing the storage performance also enhances the storage performance for metadata. During the storage of metadata, the content-related relevance of individual information elements to be stored is checked and these are either not stored, stored in part or stored as complete new data records.

Further advantageous variants of embodiments of the invention emerge from the specification.

BRIEF DESCRIPTION OF THE DRAWINGS

The present invention will become more fully understood from the detailed description of preferred embodiments given hereinbelow and the accompanying drawing, which is given by way of illustration only and thus are not limitative of the present invention, and wherein.

DETAILED DESCRIPTION OF THE PREFERRED EMBODIMENTS

Figure 1:
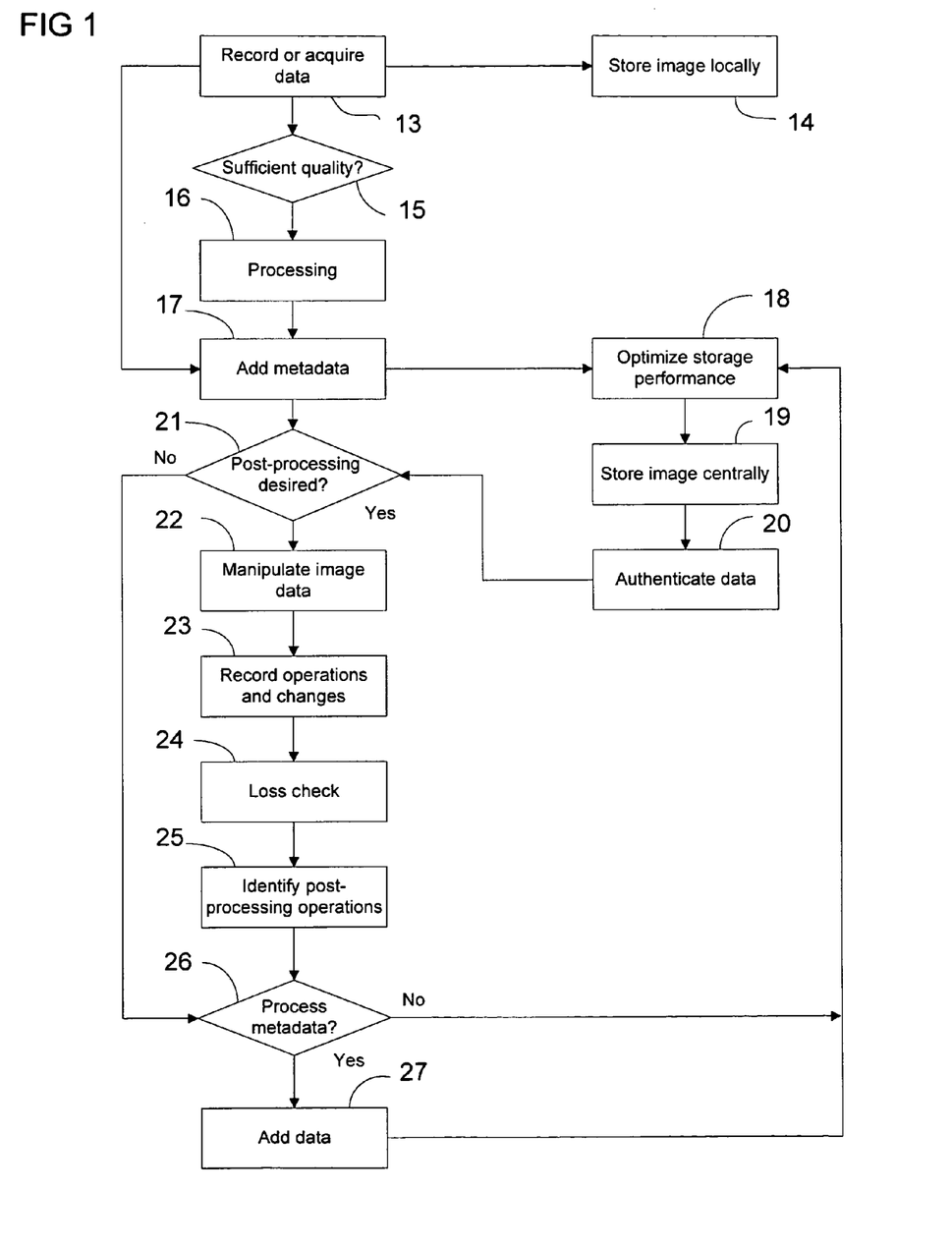
FIG. 1 shows the method of operation of the data management system of one embodiment, as a flow diagram.

FIG. 1 illustrates the method of operation of the data management device of one embodiment, as a flow diagram. The flow diagram describes the use of the device for managing medical diagnosis image and findings data.

In the initial step 13, first of all the medical image data are recorded or acquired by use of an imaging method, which proceeds e.g. in an X-ray device, a computer tomograph or an ultrasound device. In this case, the imaging method obtains raw image data which are initially present in an unchanged and therefore lossless volume of data.

The raw image data obtained by the imaging method are stored locally directly after their recording in the imaging device in step 14. The local storage increases the reliability of the method against data losses occurring later. Apart from this case, a later use of the locally stored raw image data is not envisaged. An indication of the origination date may be stored together with the raw image data.

In step 15, it is determined whether the raw image data obtained by the imaging method have a sufficient graphical quality or whether the raw image date should be conditioned by a standardized post-processing method. The standardized post-processing method represents a lossless post-processing in which, therefore, no loss of information content occurs.

Depending on the result of the check in step 15, the raw image data are either subjected to a standardized, lossless post-processing in step 16 or passed directly to step 17 of the method. In step 17, the raw image data are identified as original and lossless data and metadata such as a file identifier, an indication of the storage date or patient information are added.

In step 18, the identified raw image data and metadata are fed to an inference machine in which the data are examined with regard to optimizing the storage performance. For this purpose, the inference machine is provided with one part which accesses a knowledge base having expert knowledge about the optimum storage of image data, and with a further part which accesses a knowledge base having expert knowledge with regard to the optimum storage of metadata.

The inference machine selects suitable graphical and metadata storage formats with the aid of the two knowledge bases. In addition, the inference machine searches the metadata for specific items of information, such as patient name, patient age and technical terms of medical findings. Data constituents which can be categorized in this way are inserted into a storage scheme that is optimized in this regard, data constituents which are recognized to be irrelevant in this way are rejected, and data constituents that cannot be assigned may additionally be stored as other information items, if appropriate together with an indication of the storage data.

While the optimization of the image data primarily serves to reduce the storage requirement, the optimization of the metadata and the adaptation thereof to predetermined storage schemes pursues the aim of the checking and changing of the descriptive data being able to be systematically detected and likewise systematically reproduced by different persons and at different points in time. The metadata generally do not contain complete findings, but rather identifications such that what is involved is an image in which a specific finding can be recognized particularly distinctly. The metadata typically also contain indications of the body region examined. Metadata which include demographic information are also particularly important, since changing the latter (e.g. the patient name) entails changing the unique identifier of the patient (e.g. the patient identifier UID in the medical data format DICOM) and the assignment of the image data to the relevant person has to be corrected.

The information categories and the storage schemes are selected such that the assignment to different users and to different chronological points in time is preserved. By way of example, it is possible to use a matrix-like storage scheme whose different rows correspond to different points in time and whose columns represent different standard findings information; if appropriate, entries of different users may be included in a third dimension of such a matrix.

The image data and metadata that have been optimized with regard to the storage performance in step 18 are subsequently stored in an archive in step 19, if appropriate together with time indications. In step 19, all available information is stored centrally.

If data are intended to be taken from the central archive store for the purpose of later processing or findings then the user and archive data must firstly be authenticated in step 20 in order to ensure reliable protection against unauthorized use of the archive data and against mistakes during the removal of archive data. For this purpose, it is possible to have recourse to electronic signatures in a known manner, which releases specific archive data for processing or consideration by specific users. Furthermore, it is possible to have recourse, likewise in a known manner, to data security systems using keys which are managed by means of personal identification words or public key managements, so-called trust centers. Through the use of such security systems, the removal of archive data can be protected to the desired degree of security against misuse. This protection is of great importance particularly in the case of medical data.

The raw image data identified in step 17 or the image data and metadata removed from the archive store by way of step 20 are examined by a user in step 21 to ascertain whether an individual image post-processing is desired. If this is the case, an individual image post-processing, in which the image data can be manipulated as desired by the user, is effected in step 22. The user is in particular not bound to take possible loss of information into consideration, but rather can revise the image data in accordance with any desires.

In step 23, the graphical post-processing operations and changes to the metadata that are performed by the user are recorded as such, if appropriate with an indication of the revision date. This does not mean that, for instance, the altered image data or metadata are recorded, but rather that those operations by which the altered image data are generated are recorded. Depending on the type and scope of the post-processing operations, the later storage outlay thereof may turn out to be significantly lower than the storage requirement when storing complete image data.

In step 24, the sequence of recorded post-processing operations is examined by an inference machine to ascertain whether they lead to a lossless or lossy change in the image data or significant change in the metadata. It is thus ascertained whether losses of information occur as a result of the post-processing operations. In order to ascertain this, the inference machine accesses suitable knowledge bases with regard to graphical image processing and changing of metadata which contain rules and facts on the basis of which it is possible to weigh up between storage requirement and post-processing time requirement. It is thus ascertained in each case whether the currently revised data are lossy with respect to the original data, that is to say the data state directly prior to processing.

Examples are given below of the functioning of the knowledge-based system in step 18 and in step 24, which are based on the programming language Prolog. It goes without saying that any other programming language, such as C or C++ for example, could also be used.

The method calls and parameters of the recorded processing steps are transferred to the knowledge-based system for example as nested lists:

([method_name(someop1),in_file(a),out_file(b),
window_operator(c)],
([method_name(someop2),in_file(a),out_file(a),
window_operator(laplace)]]

After the transfer, the individual processing steps from the transferred list are checked in respect of whether at least one processing step in the sequence has a specific property (predicate) which will be designated by the variable P hereinafter. The predicate P may for example be characteristic of image processing steps:

property_existence_ps([Head|Tail],P):-apply(P,Head).
property_existence_ps([Head|Tail],P):-property_
existence_ps(Tail,P).

By way of example, local graphical image processing steps are possible as post-processing steps to be checked. For edge enhancement and smoothing, for example, the predicate P would then read "local_ip_operation" (local image processing operation), the first argument designating the method name, and the second designating the operator:

local_ip_operation(edgeEnhancement,laplace).
local_ip_operation(edgeEnhancement,sobel).
local_ip_operation(edgeEnhancement,prewitt).
local_ip_operation(smooth,gauss).

Afterward, the post-processing steps have to be checked for example in respect of whether a lossy or lossless processing of the raw data or image data that have been post-processed in a standardized manner has taken place. An associated rule can be used for the check of whether a lossy processing step is involved. This is the case for example when the combination of method name and operator is to be found under the facts of the lossy local image processing steps and the file is overwritten:

lossy(method_name(P),in_file(IN),out_file(OUT), window_operator(PV)):—local_ip_operation(P,PV),
IN=OUT.

Over and above the check of individual processing steps, it is possible, by calling the destination property_existence_ps([[method_name(someop),
in_file(a),out_file(b),window_operator(c)],[method_
name(edgeEnhancement),
in_file(a),out_file(a),window_operator(laplace)]],lossy).

to check whether at least one of the processing steps within the sequence has a specific property (property existence processing sequence, in the example "lossy"). Property and predicate can be selected freely in this case.

In a similar manner, the sequence of processing steps can be checked in respect of whether calls of compression methods are contained therein. In this example, the facts contain the method name as sole argument:

compression_method(jpeg_1s).
compression_method(jpeg_baseline).
compression_method(jpeg_2000).

Depending on the parameters, compression operations may be lossy or lossless, such as JPEG LS, for example. Examples are specified below of rules for checking whether the JPEG LS compression has taken place in a lossless manner or in a lossy manner. The JPEG LS compression is lossless if the difference between each sample value of the reconstructed data stream and the corresponding value of the original data stream is equal to 0 (DELTA=0):

lossless(method_name(P), in_file(IN),out_file(OUT),
delta(DELTA)):-P='jpeg_ls',DELTA=0.

The JPEG LS compression is lossy if the difference is not equal to 0 and the file is overwritten:

lossy(method_name(P) ,in file(IN),out_file(OUT),delta
(DELTA)):-P='jpeg_ls',DELTA>0, IN=OUT.

In an analogous manner, the sequence of processing steps can be checked for further lossy and other operations with any desired properties by means of suitable calls of destinations using property_existence_ps/2.

A further example utilizes the facts of compression_method/1 for checking transcoded image data and other data streams. A compression is lossy for all the facts presented in the facts of compression_method/1 if the spatial resolution (SPATIALRES) of the resulting data stream is lower (less than 100%) than that of the original data stream and the file is overwritten. This results in the following rule:

lossy(method_name(P), in_file(IN),out_file(OUT),delta
(DELTA), spatial_res(SPATIALRES)):-compression_
method(P),IN=OUT,SPATIALRES<100.

If a file is not overwritten directly, but rather in time-offset fashion through subsequent operations (e.g. through the contents of a buffer), then this situation can also be controlled by the suitable choice of rules which can be used to prevent an overwriting with lossy data.

Further examples for the processing of metadata are specified below. Metadata can be checked for example to determine whether demographic data have been overwritten, so that an allocation of a new object identifier becomes necessary. For this purpose, facts for different write operations are incorporated into the knowledge base, for example, where the argument designates the method name:

write_access(update).
write_access(write).

Furthermore, facts which identify corresponding DICOM attributes as tags for the identification of patients or persons are incorporated into the knowledge base. In the following example, the argument designates the DICOM tag:

patident_tag(00100010). % Patient's Name
patident_tag(00100020). % Patient ID

The associated rule assign_new_uid specifies whether a new object identifier has to be allocated. This is necessary when the method is a write operation with regard to an attribute which is relevant to the identification of patients or persons and the current attribute value differs from the original value:

assign_new_uid(method_name(P), file_id(ID),tag(TAG), datatype(DT), current_value(CV),new_value(V)):-write_access(P),patident_tag(TAG),V\=CV.

The sequence of processing operations can be checked by subsequent enquiry as to whether at least one operation which requires the allocation of a new object identifier is contained:

property_existence_ps([[method_name(update), file_id (12345),tag(00100020),datatype(longint), current_value(12990),new_value(45123)]], assign_new_uid).

This example shows that property_existence_ps/2, through the suitable choice of predicates for the second argument, can be used to check not just one but a plurality of different properties.

Examples are given below of rules which serve to optimize the storage performance. For this purpose, the knowledge-based system has a knowledge base with facts and rules for supporting the decision as to whether revised data or only the sequence of the recorded processing operations are intended to be recorded. In this case, there is a weighing up between time requirement for the reconstruction of the revised data and storage requirement. In this case, reconstruction refers to the later process of effecting accessibility and representation on data processing devices or else on paper or in some other way.

Depending on the type of data and processing steps, it may turn out that the reconstruction of the revised data from the original, unprocessed data together with associated processing steps or else from the processed data themselves is more favorable. In this case, the storage of the processed data themselves, particularly in the case of image data, needs a higher storage requirement, while the subsequent reconstruction from the processing steps causes a higher computational complexity.

The following example contains facts and rules for the relatively time-consuming operations of 3D region growing and the manual marking of regions of interest (ROI). The two operations are categorized as follows as facts for contour operations:

contour_operation(three_d_region_growing).
contour_operation(mark_roi,manual).

One of the rules in connection with the optimization of the storage performance states that the revised data (e.g. an isolated segmented object) are intended to be stored (store object) if the operation is a 3D region growing method. The reason for this is that it is generally more favorable to store the result of the segmentation than to comprehend the region growing operation:

store_object(object(O),method_name(P)):-
  P='three_d_region_growing'.

A further rule specifies that the sequence of processing steps is intended to be stored (store processing sequence=store_ps) if an operation that is classified as a contour operation and has the method name 'mark_roi,' is involved. In this case, 'mark_roi' denotes an operation by which the contour of a region of interest is marked (e.g. by means of a polygon progression). Even though for example the manual marking of the contours may be very time-consuming, it is possible to store the result of the manual segmentation in the processing sequence of the data without duplicating the original data in the process. If appropriate, the result of 'mark_roi' could also be stored as a separate overlay object.

store_ps(object(O),method_name(P),mode):-contour_operation(P,M) P='mark_roi'.

Finally, the sequence of the post-processing operations can be checked in respect of whether at least one operation which necessitates the storage of additional objects has been carried out:

property_existence_ps([[object(12404), method_name (mark_roi,mode(manual))]],store_object).

In step 25, an identification of the post-processing operations is effected in a manner dependent on the preceding loss check by the inference machine to ascertain whether the operations lead to a lossless or to a lossy alteration of the image data. This identification thus makes it possible to ascertain for example whether, after the post-processing of raw image data, only a purely structurally revised version of these data is present, which, however, can still be regarded as raw image data, or whether a version that has also been revised in terms of the information content has been generated. The user often cannot make this distinction at all himself in view of the highly complex automatic image processing operations that are possible nowadays. Therefore, he could neither perform the identification himself nor store the data in a manner adapted thereto. Apart from this, work is facilitated significantly for the user if he does not have to concern himself with this distinction in the first place.

In step 26, the post-processed data or data taken from the archive are checked by the user to determine whether findings or comments on the data are to be effected, that is to say a processing of the metadata contained in the data. If this is the case, findings or commentaries added by the user are added to the data in step 27. In addition to the entries by the user, information which allows the user to be identified, e.g. by way of his electronic signature, is also added to the metadata. The user's entries may contain for example the particular relevance of an image with regard to specific medical findings or other diagnostic data associated with the image data.

The post-processed image data and supplemented metadata are returned to step 18 of the method, where they are once again fed to the archive storage, if appropriate together with indications of the revision or storage date. The inference machine in step 18 decides, as described above, about suitable graphical storage formats and also a suitable systematic metadata storage. In this case, the decision about a suitable graphical storage format takes account of the fact that the image data are available on the one hand as image information per se, but also, on the other hand, as a sequence of image post-processing operations. Thus, a decision is made not only about the storage in pure graphical data formats, but also about an extended storage format taking account of image processing operations. Furthermore, the supplementary information entered by the user is also examined with regard to its information content and subordinated to a suitable storage scheme. In this case, it is possible e.g. to take account of the fact that a commentary that is identical in each case at different points in time must not be repeatedly and multiply stored.

Figure 2:
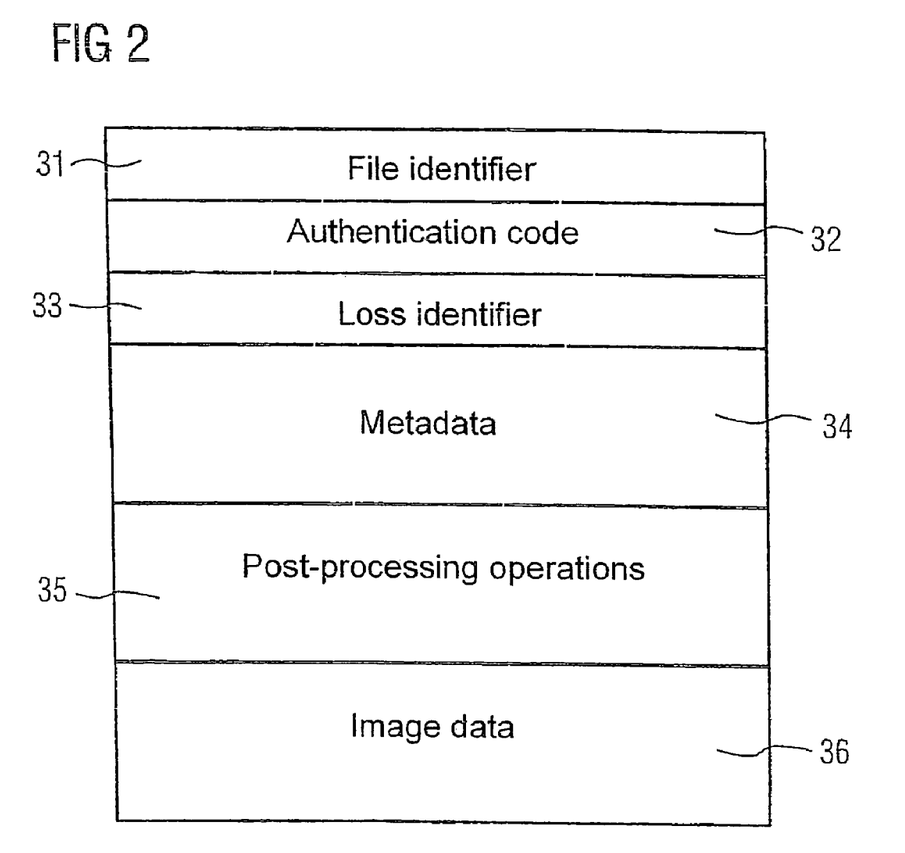
FIG. 2 shows a data structure generated by the data management system of one embodiment.

FIG. 2 illustrates the data structure provided by an embodiment of the invention. The illustration shows an information block subdivided into individual information elements. The data structure may be stored as a file or as a distributed, networked file system. The individual structure elements are data-technologically subdivided or separated from one another by markers, but do not have a fixedly predetermined size. In particular, it is possible for individual structure elements of the data structure to remain without information, i.e. empty.

Structure element 31 of the data structure is a file identifier, comparable to a file name, which serves for the assignment of and the ability to find the data structure in a file storage system. The file name may be allocated in a known manner such that it is generated systematically and provided with an indication e.g. of the examined patient.

Structure element 32 contains an authentication code which may be used for data protection purposes. By use of the authentication code, the processing and use of the data structure can be enabled only for specific users. Moreover, additional security may be provided by the actually desired data structure being made available to the user. There may be a key contained which releases the data structure only to users who have a matching further key.

Structure element 33 contains an identification which gives information about whether the data in the data structure are obtained in a lossless manner or are post-processed in a lossy manner. The identification may be multipartite insofar as it is possible for the data structure to contain both lossless raw data and lossy post-processed image data and metadata and graphical post-processing operation data. In such cases, it is possible to take either the raw data or the post-processed data from the data block. The plurality of processing states of the image data that are present, if appropriate, may either be represented simultaneously of be presented in chronological order or in a manner overlaid over one another by a suitable user interface. If the data structure only contains data in a single processing status, then the identification in constituent 33 is also in a single stage and merely gives information about the individual data status present.

Structure element 34 contains metadata such as findings data or commentaries. The metadata are present in tabular form and in the form of text information which is entered in part automatically by the system and in part manually by the user. The metadata contain all relevant information in connection with the image data regarding the patient, the circumstances of obtaining images and, if appropriate, aspects of the medical findings. The metadata may be in multiple stages insofar as they can be entered at different points in time and by different users.

Structure element 35 contains a sequence of post-processing operations to which the image data have been subjected by one or different users. Thus, what is involved is not image data per se, but rather information about the way in which the image data have been altered in each case. The fact of whether post-processing operations are stored depends essentially on whether the result of image post-processing operations is thereby to be stored and handled the most efficiently. The sequence of post-processing operations contained in structure element 35 may also be stored as a dedicated object which references the image data to which the operations have been applied. This is advantageous if a relatively large number of images have been post-processed in the same way.

Structure element 36 contains, as central object of the data structure the actual image data, which may be present either as raw image data or in a form that has been revised already in a standardized manner or in a nonstandardized manner. The image data may be lossless or lossy.

The data structure illustrated in FIG. 2, with full utilization of all the options, could contain the results of an imaging examination of a patient together with complete pathogenesis and complete findings over a relatively long examination period and with consultation of the assessments of a number of experts.

Figure 3:
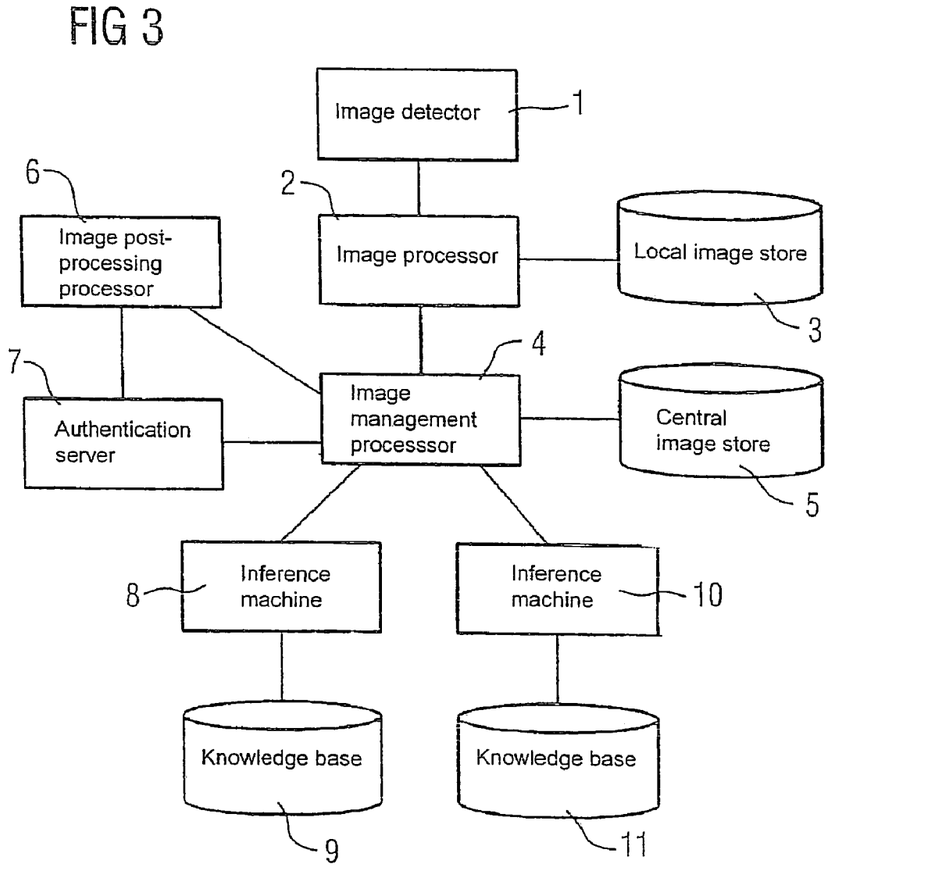
FIG. 3 shows a system architecture of the data management device of one embodiment.

FIG. 3 illustrates the system architecture required for implementing an embodiment of the invention. The data management system illustrated receives image data from an image detector 1. The image data pass to an image processor 2, which brings the image data to a format which is suitable for their processing, storage or graphical representation on an output device.

Depending on the quality of the image data, the image processor 2 may additionally perform a standardized image post-processing during which the image data are post-processed in a lossless manner for the purpose of better further usability. The image data that have been post-processed in a standardized manner, if appropriate, pass from the image processor 2 to a local image store 3. The local image store 3 only has a security function insofar as it serves to immediately save recorded image data until the final, central storage thereof.

The image data processed by the image processor 2 further pass to an image management processor 4, which centrally manages, stores and archives the image data. The storage of the data by the image management processor 4 is effected in the central archive image store 5.

The centrally archived image data can be retrieved from the image management processor 4 by an image post-processing processor 6. In this case, the authorization for retrieval of the data and the ensuring of the identity thereof are ensured by an authentication server 7, accessed by both the image post-processing processor 6 and the image management processor 4. The authentication server 7 has knowledge of those electrical signatures by which the image archive is permitted to be accessed by the image post-processing processor 6, and also keys which are interrogated during the access. The authentication server 7 thus ensures that only authorized users can access only the data released to them.

The image management processor 4 accesses an inference machine 8, which is able to check post-processed image data to determine whether the post-processing has been effected in a lossless manner or in a lossy manner. For this purpose, the inference machine 8 has access to a knowledge base 9 containing expert knowledge with regard to the examination of data for a lossless or lossy status. The image management processor 4 additionally accesses an inference machine 10, which is able to find a storage format for optimizing the storage performance. For this purpose, the inference machine 10 accesses a knowledge base 11 containing expert knowledge regarding the question of storage optimization of image and text data. It is also possible to use, instead of two inference machines 8, 10, just one which accesses the two different knowledge bases 9, 11.

By consulting the check results of the inference machine 8, the image management processor 4 is able to provide the data to be stored with an identification which gives information about whether the data have been post-processed in a lossy manner or obtained in a lossless manner. In conjunction with the optimization of the storage performance by the inference machine 10, the data management processor 4 can thereby ensure that original image data are obtained in a lossless manner and can be stored together with post-processed data or data supplemented by text information with a minimal storage outlay and with retention of information about the storage history.

A data structure for storing image data and metadata, may further include a structure part for a file name; a structure part for unprocessed or processed image data; a structure part for unprocessed or processed metadata; and a structure part for an identification which gives information about whether the stored data were obtained in a lossless manner or are lossy in comparison with the original data.

Further, a storage medium may include information items, wherein the information items are adapted to interact with a data processing device to perform any of the methods set forth above. The storage medium may be a built-in medium installed inside a computer or other data processing device main body, or removable medium arranged so that it can be separated from the computer or other data processing device main body. Examples of the built-in medium include, but are not limited to, rewriteable involatile memories, such as ROMs and flash memories, and hard disks. Examples of the removable medium include, but are not limited to, optical storage media such as CD-ROMs and DVDS; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for storing data, comprising:
   an electronic data processing device, adapted to process the data;
   data loss check means for checking processed data for data loss in comparison with original data;
   an electronic data management device, adapted to convert the processed data to a format suitable for storage in a manner dependent on the result of the check performed by the data loss check means;
   a storage device, adapted to store the data, wherein the storage device is adapted to store lossy data in addition to data obtained in a lossless manner; and
   storage optimization means for weighing up time and storage outlay for the subsequent reconstruction of revised data from the original data together with the associated processing steps, against the time and storage outlay for the subsequent reconstruction of revised data from the processed data, and wherein, depending on the result of this weighing up, at least one of the original data together with the associated processing steps and the processed data are stored in the storage device,
   wherein the data includes at least one of image data and metadata.

2. The apparatus of claim 1, further comprising:
   recording means for recording processing steps during the processing of the data.

3. The apparatus of claim 2, wherein at least one of the lossless and lossy data are storable together with an identification with regard to a point in time of the data state.

4. The apparatus of claim 1, wherein at least one of the lossless and lossy data are storable together with an identification with regard to a point in time of the data state.

5. A method for generating a data structure with at least one of unprocessed data and processed data, comprising:
   determining whether the processed data was obtained in a lossless or lossy manner in comparison with the unprocessed data using an electronic data processing device;
   adding an identification, dependent on the result of the determining, to the data structure;
   recording processing steps carried out during processing of the data; and
   storing one of the processed data and the unprocessed data together with the processing steps carried out during revision in a storage device, depending on whether subsequent reconstruction of revised data from the unprocessed data and the associated processing steps involves less time and storage outlay than the subsequent reconstruction of the revised data from the processed data,
   wherein the data includes at least one of image data and metadata.

6. The method of claim 5, further comprising:
   storing at least one of lossless and lossy data together with an identification indicating a point in time of the data state.

7. The method of claim 5, further comprising:
   assigning a file name to the data structure; and
   storing the data structure in a storage medium.

8. A computer readable medium encoded with computer program instructions for generating a data structure with at least one of unprocessed data and processed data, which when executed on a computer, cause the computer to execute the instructions comprising:
   determining whether the processed data was obtained in a lossless or lossy manner in comparison with the unprocessed data;
   adding an identification, dependent on the result of the determining, to the data structure;
   recording processing steps carried out during processing of the data; and
   storing one of the processed data and the unprocessed data together with the processing steps carried out during revision, depending on whether subsequent reconstruction of revised data from the unprocessed data and the associated processing steps involves less time and storage outlay than the subsequent reconstruction of the revised data from the processed data,
   wherein the data includes at least one of image data and metadata.

9. The computer readable medium of claim 8, wherein the instructions further comprise:
   storing at least one of lossless and lossy data together with an identification indicating point in time of the data state.

10. The computer readable medium of claim 8, wherein the instructions further comprise:
    assigning a file name to the data structure; and
    storing the data structure in a storage medium.

* * * * *